United States Patent [19]

Corvi Mora

[11] Patent Number: 4,596,894
[45] Date of Patent: Jun. 24, 1986

[54] MIXTURE OF DIASTEROISOMER COMPOUNDS, AS OBTAINED FROM (−)-5-(1-HYDROXY-1-METHYLETHYL)-2-METHYL-2-CYCLOHEXENE-1-ONE, HAVING MUCOSECRETOLYTIC ACTIVITY, A PROCESS FOR ITS PREPARATION AND PHARMACEUTICAL COMPOSITIONS CONTAINING THE SAME

[75] Inventor: Camillo Corvi Mora, Milan, Italy

[73] Assignee: Camillo Corvi S.p.A., Italy

[21] Appl. No.: 746,559

[22] Filed: Jun. 19, 1985

[30] Foreign Application Priority Data

Aug. 8, 1984 [IT] Italy ............................. 22257 A/84

[51] Int. Cl.$^4$ ............................................. C07C 35/18
[52] U.S. Cl. ..................................... 568/823; 514/729
[58] Field of Search ......................... 568/823; 514/729

[56] References Cited

U.S. PATENT DOCUMENTS 2,949,489  8/1960  Durbetaki et al. .................. 568/823

FOREIGN PATENT DOCUMENTS 764323  8/1971  Belgium .............................. 568/823

*Primary Examiner*—Werren B. Lone

*Attorney, Agent, or Firm*—Ostrolenk, Faber, Gerb & Soffen

[57] ABSTRACT

The object of the present invention are the following diastereoisomer compounds (as derived from (−)-5-(1-hydroxy-1-methylethyl)-2-methyl-2-cyclohexene-1-one):

(I): (1S-5R) 5-hydroxy-$\alpha,\alpha$-4,5-tetramethyl-3-cyclohexene-1-methanol (CO/1516)

(II): (1S-5S) 5-hydroxy-$\alpha,\alpha$-4,5-tetramethyl-3-cyclohexene-1-methanol (CO/1517)

which can be separated from the mixture of (I)+(II) at the % proportion of 44.44/55.55; said mixture will be hereinafter also designated either by the code CO/1483 or by (III).

This invention provides, furthermore, the process for obtaining the mixture (III) (CO/1483) by reaction of (−)-5-(1-hydroxy-1-methylethyl)-2-methyl-2-cyclohexene-1-one with methyl-lithium and for separating the diastereoisomers (I) and (II) by a chromatographic method.

Finally, the present invention comprises pharmaceutical compositions which contain the compounds (I), (II) and the mixture (III), when possess a pharmacologic mucosecretolytic activity.

7 Claims, No Drawings

MIXTURE OF DIASTEROISOMER COMPOUNDS, AS OBTAINED FROM (−)-5-(1-HYDROXY-1-METHYLETHYL)-2-METHYL-2-CYCLOHEXENE-1-ONE, HAVING MUCOSECRETOLYTIC ACTIVITY, A PROCESS FOR ITS PREPARATION AND PHARMACEUTICAL COMPOSITIONS CONTAINING THE SAME

The object of the present invention are the following compounds:
(1S-5R)5-hydroxy-α,α- 4,5-tetramethyl-3-cyclohexene-1-methanol (CO/1516) having the structural formula:

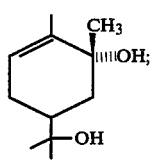
(I)

$C_{11}H_{20}O_2$ mol.wt.184.28, m.p.114°–116° C.
(1S-5S 5-hydroxy-α,α-4,5-tetramethyl-3-cyclohexene-1-methanol (CO/1517) having the structure formula:

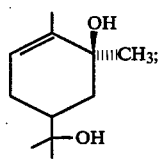
(II)

$C_{11}H_{20}O_2$ mol.wt.184.28, m.p.101°–104° C.
The mixture (III) consists of 55.55% of compound of formula (II) (CO/1517) and 44.44% of compound of formula (I) (CO/1516) with m.p. 77°–100° C. (CO/1483).

The starting compound for the preparation of the active substances which are the subject of this invention is the (−)-5-(1-hydroxy-1-methylethyl)-2-methyl-2-cyclohexene-1-one.

Said compound, well known in the literature, has the structural formula:

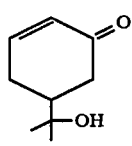
(IV)

(−) $C_{10}H_{16}O_2$ mol.wt.168,235
and is named carvone hydrate, hydroxycarvotan-acetone (Rupe and Schlochoff, Ber. 1905 Vol. 38 page 1719; Harry Schmidt, Chem. Ber. 1953, 11, page 1442). The above substance, being not commercially available, has been synthetized by a process of oxidizing (−)trans-5-hydroxy-α,α-4,5-trimethyl-3-cyclohexene-1-methanol ( (−)-trans-sobrerol), by means of Jones reagent:

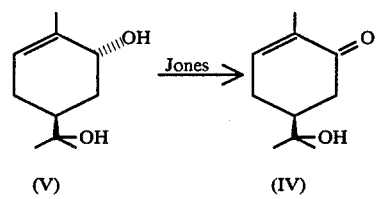

according to the following method:

Method for preparing the starting compound (−)-5-(1-hydroxy-1-methylethyl)-2-methyl-2-cyclohexene 1-one of formula (IV)

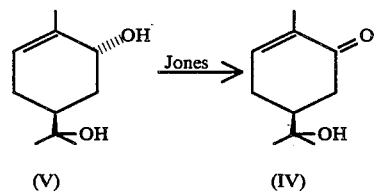

20g of (−)trans-sobrerol are suspended in 800 ml acetone; while cooling in ice water, are added by slowly dropping, under vigorous mechanical stirring (which is important because the chromium salts which precipitate, tend to incorporate some of the starting sobrerol) to 55 ml of Jones reagent*(until a persistent orange colouring). Stirring is continued for about 1 hour, the excess chromium (IV) is destroyed by isopropanol (the mixture turns again to a dark green colour) and the mixture is diluted with demineralized water. The mixture is extracted thoroughly (4×500ml) with ethyl acetate, dried over $Na_2SO_4$, evaporated to dryness and chromatographed on 400g of silica gel by eluting with 3:1 cyclohexane/ethyl acetate. 14g of (−)-5-(1-hydroxy-1-methylethyl)-2-methyl-2-cyclohexene-1-one is obtained.

* Jones reagent
26.72 of $CrO_3$ are dissolved in 45ml of water, 23ml concentrated $H_2SO_4$, while stirring, are added cautiously and the mixture is taken to 100ml with water.

SYNTHESIS SCHEME OF CO/1483 [CO/1516 + CO/1517]

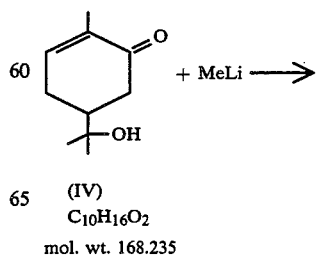

(IV)
$C_{10}H_{16}O_2$
mol. wt. 168.235

-continued
SYNTHESIS SCHEME OF CO/1483 [CO/1516 + CO/1517]

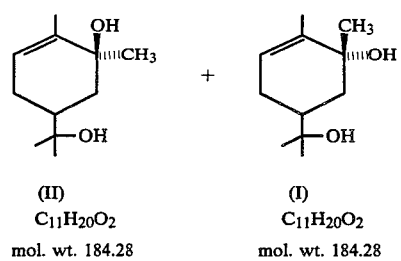

(II)
C₁₁H₂₀O₂
mol. wt. 184.28

(I)
C₁₁H₂₀O₂
mol. wt. 184.28

EXAMPLE 1
Preparation of mixture (III) ( CO/1483)

To a solution of 10g of (−)-5-(1-hydroxy-1-methylethyl)-2-methyl-2-cyclohexene-1-one in ethyl ether,- cooled to −30° C., slowly and under stirring are added 100 ml of a 5% methyllithium solution in ethyl ether. The mixture is left under stirring at room temperature for 12 hours, it is diluted with water and the ethereal phase is separated, which phase is washed again with water, desiccated over anhydrous sodium sulphate and evaporated to dryness. The residue is subdivided in isopropyl ether, to obtain 9g (82%) of the product as a mixture of diastereoisomers (m.p. 77°-100° C.). These are separated by chromatography on a silica gel column, by eluting with 6:4 cyclohexane/ethyl acetate. There are obtained 5g of a product of higher Rf (CO/1517), with m.p. 101°-104° C., and 4g of a product of lower Rf (CO/1516), with m.p. 114°-116° C.

CO/1517

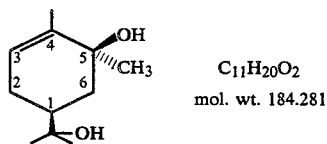

C₁₁H₂₀O₂
mol. wt. 184.281

(II)

IR (nujol dispersion; cm⁻¹): 3440 and 3360 ν OH: 1163; 1088; 1003; 989; 920; 810 characteristic bands NMR (90 MHz, solvent: CDCl₃; TMS reference; δppm): 5.39 centre c.a. (1 H CH); 2.15÷1.35 c.a. (8 H; CH₂—CH—CH₂and CH₃—C=); 1.33 s (3 H; CH₃—C—OH); 1.2 s (6 H; gem CH₃)

c.a.=complex absorption s=singlet TMS=tetramethylsilane

NMR (300 MHz , CDCl₃ solvent): C₍₅₎—CH₃ₐₓ, 6Hₐₓ=0.75 Hz (typical trans-diaxial coupling)

MS (quadrupole, electronic impact, direct insertion, (80 eV, and 80 mA, m/z): 156 [(M-18)⁺, 14%]; 151 [(M-18-15)⁺, 24%]; 133 (6%); 123 (24%); 111 (7%); 110 (6%); 109 (58%); 108 (52%); 107 (30%); 105 (5%); 95 (18%); 94 (10%); 93 (81%); 91 (22%); 83 (12%); 81 (15%); 79 (12%); 77 (17%); 67 (15%); 59 (base peak)

| Elemental analysis | | |
|---|---|---|
| Calculated: | | |
| C = 71.70% | H = 10.94 | O = 17.36 |

| Elemental analysis | |
|---|---|
| Found | |
| C = 71.80 | H = 10.87 |
| 71.89 | 10.79 |
| 71.81 | 10.82 |

CO/1516

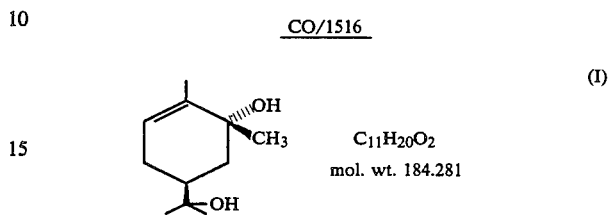

C₁₁H₂₀O₂
mol. wt. 184.281

(I)

IR (nujol dispersion; cm⁻¹): 3310 νOH; 1285; 1150; 1086; 1059; 973; 923; 874; 811 characteristic bands NMR (90 MHz; solvent : CDCl₃; TMS reference; δppm): 5.47 centre c.a. (1 H, CH =); 2.3÷1.1 c.a. (7 H, CH₂—CH—CH₂and C=C—C—OH and (CH₃)₂—C—OH); 1.73 b.s. (3 H, CH₃—C=C); 1.3 s. (3 H, C=C—C—CH₃); 1.2 and 1.17 2 s. (6 H, gem CH₃)

TMS=tetramethylsilane s.=singlet 2 s.=2 singlets c.a.=complex absorption b.s.=broadened singlet MS (quadrupole; direct insertion; electronic impact 80 eV; 80 mA; m/z): 169 [(M-15)⁺; 1%]; 166 [(M-18)⁺; 5%]; 151 [(M-18−15)⁺; 17%]; 148 (3%); 133 (3,5%); 123 (23%); 111 (6%); 109 (43%); 108 (13%); 107 (12%); 105 (4%); 95 (9%); 93 (39); 91 (12%); 83 (10%); 81 (9%); 77 (11%); 67 (11%); 59 (base peak).

Unexpectedly, it has been found that, if (−)-5-(1-hydroxy-1-methylethyl)-2-methyl-cyclohexene-1-one, the preparation of which has been previously disclosed, is treated with methyllithium in an aprotic solution, it converts to a mixture of diastereoisomers (CO/1483) (III), which is one of the objects of the present invention. The mixture, furthermore, can be separated to the individual components (I)=CO/1516 and (II)=-CO/1517 by a chromatographic process.

Also the components (I) and (II), the analytical identifications of which have been provided above, are an object of the present invention.

Mixture (III) and its components (I) and (II), when subjected to pharmacological screening, showed interesting mucolytic properties on the bronchial secretion, which designate them as potential drugs which may be applied in the therapy of bronchopneumonic diseases.

TABLE 1
BRONCHOSECRETAGOGUE ACTIVITY OF CO/1483

Below are reported the average values of percent increase of the bronchial mucus secretion by treatment with CO/1483 as well as other known standards as compared to the basal values. Further, there is reported the number of rabbits which showed an increase of bronchial secretion as compared with all the animals treated with CO/1483 at the varying doses and via the two administration routes (R. Scuri et al, Boll. Chem. Farm., 119, 187-7, 1980).

| Dose in mg/kg | Administration way | Bronchial secretion average increase, | N° of rabbits with a secretion increase/N° of rabbits treated |
|---|---|---|---|
| CO/1483 | | | |
| 100 | oral | 35 | 5/13 |
| 200 | oral | 59 | 7/13 |
| 400 | oral | 104 | 9/13 |
| N—acetylcysteine | | | |
| 400 | oral | 22 | 8/16 |
| 600 | oral | 59.4 | 6/9 |
| Bromhexine | | | |
| 200 | oral | 35.8 | 4/8 |
| 400 | oral | 43 | 6/8 |
| Carboxymethylcysteine | | | |
| 200 | oral | 10 | 4/10 |
| 400 | oral | 46 | 5/10 |

Referring to the activity shown by the mixture (III) (CO/1483) of (I) and (II) as mucosecretolytic agents, the present invention further provides pharmaceutical compositions which contain the compound (III) in dosage unit. Pharmaceutical forms containing the above mentioned mixture of active ingredients, may be for example, the injectable forms and those for aerosol, as well as the ones for oral administration, in particular, capsules, tablets, granular forms in sachets, syrups and forms for rectal administration (suppositories).

In the forms as mentioned, conventional excipients are combined with mixture (III).

In the solid oral forms (tablets, capsules, granular forms) the preferred excipients are: lactose, starch, cellulose and its derivatives, with all the carrier materials for the preparation of the pharmaceutical form, such as precipitated silica, talc, calcium or magnesium stearate.

In the form of syrup, the active compound is dissolved in a sugar solution (saccharose, glucose, sorbitol) with addition of aromatizing and preservaing agents.

In the form of suppositories, the main excipient consists of triglycerides of fatty acids, either pure or as a mixture with oxyethylated derivatives.

In the injectable or aerosol forms, the mixture (III) is brought to an isotomic solution and either cold or hot sterilized.

I claim:

1. (1S-5R)-5-hydroxy-α,α-4,5-tetramethyl-3-cyclohexene-1-methanol.

2. (1S-5S)-5-hydroxy-α,α-4,5-tetramethyl-3-cyclohexene-1-methanol.

3. A mixture of the (1S-5R) and (1S-5S) diastereoisomers of 5-hydroxy-α,α-4,5-tetramethyl-3-cyclohexene-1-methanol, in which the (1S-5R) compound is present in the amount of 44.44% and the 1S-5S compound is presented in the amount of 55.55%.

4. A process for the preparation of the mixture of the diastereoisomers according to claim 3, characterized in that (−)-5-(1-hydroxy-1-methylethyl)-2-methyl-2-cyclohexene-1-one, in ethyl ether, is reacted, at −30° C., with an ether solution of 5% methyllithium, then the reaction mixture is stirred continuously for 12 hours at room temperature, washed with water, evaporated to dryness, purified with isopropyl ether, thereby yielding the diastereoisomers mixture.

5. The process of claim 3 characterized in that the diastereoisomers of the mixture are separated by chromatography on a silica gel column, eluting with 6:4 cyclohexane/ethyl acetate.

6. A pharmaceutical composition having mucolytic activity on the bronchial secretion, characterized by the mixture of diastereoisomers according to claim 3 and a pharmaceutically acceptable carrier.

7. A method of increasing bronchial mucous secretion which comprises administering to a host an effective bronchial mucolytic secretion amount of the mixture of claim 3.

* * * * *